(12) United States Patent
Dion (10) Patent No.: US 10,959,422 B2
(45) Date of Patent: Mar. 30, 2021

(54) SCENTING DEVICE HAVING DISTANCE MARKERS

(71) Applicant: Cary D. Dion, San Diego, CA (US)

(72) Inventor: Cary D. Dion, San Diego, CA (US)

( * ) Notice: Subject to any disclaimer, the term of this patent is extended or adjusted under 35 U.S.C. 154(b) by 326 days.

(21) Appl. No.: 15/967,166

(22) Filed: Apr. 30, 2018

(65) Prior Publication Data
US 2018/0310545 A1 Nov. 1, 2018

Related U.S. Application Data

(60) Provisional application No. 62/491,604, filed on Apr. 28, 2017.

(51) Int. Cl.
*A01M 31/00* (2006.01)
*A01M 1/20* (2006.01)
*A61L 9/12* (2006.01)

(52) U.S. Cl.
CPC ......... *A01M 31/008* (2013.01); *A01M 1/2044* (2013.01); *A61L 9/12* (2013.01)

(58) Field of Classification Search
CPC .............. A01M 31/008; A01M 1/2044; A01M 1/2055; A61L 9/12; G01B 3/12
USPC .......................................................... 239/48
See application file for complete search history.

(56) References Cited

U.S. PATENT DOCUMENTS

| | | | | | |
|---|---|---|---|---|---|
| 1,415,489 | A | * | 5/1922 | Simpson .............. | G01B 3/1041 242/379 |
| 1,777,820 | A | * | 10/1930 | Anenberg ............... | A24F 25/02 239/48 |
| 2,742,705 | A | * | 4/1956 | Gelardi .................... | G01B 3/10 33/758 |
| 3,120,345 | A | * | 2/1964 | Bolger ................ | A01M 1/2055 239/52 |
| 3,524,273 | A | * | 8/1970 | Shore .................... | G01B 3/1084 40/495 |
| 4,523,717 | A | * | 6/1985 | Schwab .............. | A01M 31/008 206/225 |
| 4,788,787 | A | * | 12/1988 | Konietzki ........... | A01M 31/008 239/48 |
| 4,964,744 | A | * | 10/1990 | Whitear ................. | A45D 34/04 239/48 |
| 5,494,218 | A | * | 2/1996 | Armand ................. | A47K 10/32 239/52 |
| 5,622,314 | A | * | 4/1997 | Eason ....................... | A61L 9/12 239/44 |
| 5,947,379 | A | * | 9/1999 | Freeman ............. | A01M 31/008 239/52 |
| 6,429,391 | B1 | * | 8/2002 | Gruver ................... | G01G 19/14 177/148 |
| 6,470,619 | B1 | * | 10/2002 | Snyder ............... | A01M 31/008 239/44 |
| 6,676,033 | B1 | * | 1/2004 | Campesi, Sr. ...... | A01M 31/008 239/44 |
| 6,800,252 | B1 | * | 10/2004 | Jedzinski ................... | A61L 9/12 422/123 |

(Continued)

*Primary Examiner* — Joseph A Greenlund
(74) *Attorney, Agent, or Firm* — Donn K. Harms (57) ABSTRACT

A scent dispensing apparatus having a spool engaged with a housing for dispensing a scented line upon the ground. The scented line is wound upon the spool which is positionable between a retracted position inside a cavity of the housing to a deployed position outside the housing where the spool can unwind the scented line.

11 Claims, 4 Drawing Sheets

(56) References Cited

U.S. PATENT DOCUMENTS

| | | | |
|---|---|---|---|
| 6,810,614 B2* | 11/2004 | Phillips | F41C 27/00 42/75.01 |
| 7,216,665 B1* | 5/2007 | Sims, Jr. | A61M 39/08 137/355.19 |
| 8,889,116 B2* | 11/2014 | Potgeter | A01N 25/34 424/84 |
| 9,975,668 B1* | 5/2018 | Rimmer | A01M 31/008 |
| 2006/0071092 A1* | 4/2006 | Harris, Jr. | A01M 29/12 239/44 |
| 2009/0020625 A1* | 1/2009 | Trevino | A01M 1/2044 239/44 |
| 2012/0017486 A1* | 1/2012 | Jones | G01B 3/10 42/120 |
| 2015/0060564 A1* | 3/2015 | Bowles | A61L 9/127 239/6 |
| 2015/0209392 A1* | 7/2015 | Song | A61L 15/60 424/93.3 |
| 2018/0310545 A1* | 11/2018 | Dion | A01M 31/008 |
| 2019/0094001 A1* | 3/2019 | Murray | G01B 3/1003 |

* cited by examiner

SCENTING DEVICE HAVING DISTANCE MARKERS

This application claims priority to U.S. Provisional Patent Application Ser. No. 62/491,604, filed on Apr. 28, 2017, which is incorporated herein in its entirety by this reference thereto.

FIELD OF THE INVENTION

The present device relates to the sport of hunting and to the act of positioning scent to attract game. More particularly, it relates to a spooled scenting line to which a scent may be imparted by pre-loading to the line when wound to a housing-engageable spool or with the spooled line wound to the spool while engaged within the housing. The resulting scented line is dispensable from the spool and may include visually discernable distance markers located sequentially on the line.

BACKGROUND OF THE INVENTION

In hunting, one widely employed strategy to increase success of the hunt involves locating a scent in an area of hunting interest. Conventionally the scent deployed is attractive to the prey the hunter is seeking. Because many animals have a very keen sense of smell, the deployment of scent can attract them to the location of the hunt. Various scents can be deployed to attract the game animal such as food scents, glandular scents, and bodily fluid scents such as urine from the same species of the game animal the hunter is seeking.

Consequently, hunters will frequently impart a scent to the area to be hunted using various types of scenting devices. Such positioning of a game attracting scent also serves to help mask the human hunter scent which many game animals have learned to avoid. Thus, the employment of scents to attract game and concurrently mask that of the hunter, can be very advantageous when used correctly.

Conventionally, scents for attracting game are positioned near the hiding spot of the hunter or at other desired locations proximate thereto. This allows a disguised or hidden hunter to survey the scented area to ascertain what has been attracted. Commonly employed scenting devices can be hung from trees, stuck in the ground, or tied to the trunks of trees.

Conventionally, nothing has been provided to allow hunters and other scent using individuals, to allow for standardized deployment of a scent which may be retracted and reused at a later date. Some conventional means to employ scents use wicks and sponges and rags which are dipped or sprayed with liquid scent bought in a container and placed on the ground or hung from trees. Alternatively, liquid scent may be dispensed from a spray or dripping container in various areas.

However, conventional scent imparting liquids and materials, are generally very expensive and have a significant cost to the hunter. Once deployed by spraying, dripping, or evaporated from wicks, expensive liquid scents are not reusable, and wicks and rags which are scented are not easily reused since they must be collected and stored.

The device herein provides an easy to employ, reusable scenting device and method. Through the employment of a spool deployable and retractable line which is liquid absorbent, a scent may be imparted to an area for a significant uninterrupted distance by the unwinding of a scented line upon the ground or in vegetation. Rather than small conventional wicks or liquid deposits to spaced irregular positions, the scented line herein enables the imparting of a scent continuously along an unbroken line for many yards. Such provides a significant gain in the scent carried by the wind to surrounding areas. Further, the spooled line can be dragged to a location to impart a scent that may be followed by game and may also include visually discernable distance markers positioned at determined distances thereon. When viewed from a position adjacent the deployed scented line, the markers provide the hunter a visually discernable gauge for distance determination which can be employed to ascertain distance during aiming of a bow or firearm or the like. Such distance marking which is visually discernable provides a means for the hunter to significantly increase accuracy by accommodating a known distance during aiming.

The forgoing examples of scenting as conventionally employed during hunting, and limitations related therewith, are intended to be illustrative and not exclusive, and they do not imply any limitations on the invention described and claimed herein.

Various other limitations of the related art are known or will become apparent to those skilled in the art upon a reading and understanding of the specification below and the accompanying drawings.

SUMMARY OF THE INVENTION

The device and system herein disclosed and described provides a solution to the shortcomings in prior art of scent placement during hunting. The disclosed device achieves the above noted objects through the provision of a scenting device configured to dispense and rewind a scented line which is circumferentially engaged about the exterior of a rotatable spool. The spool is engaged within an interior cavity of a housing and moveable from a retracted or stored position, sealing the line wound upon the circumference of the spool, within the cavity. The line, so positioned on the spool in the interior cavity, is thereafter located to a deployed position by translating the line out of the cavity whereupon it will unwind from the spool.

In the deployed position, the scented line unwound from the spool may be laid in an unbroken line along the ground. This forms an elongated, unbroken scenting line which may be followed by game. Once a hunting session is finished, the line may be rewound upon the spool using a handle engaged to the rotationally engaged spool, until fully rewound on the spool which is translated to a position projecting from the interior cavity. Thereafter, the spool may be translated back into the cavity of the housing thereby sealing the scented line therein with a seal engaged on one end of the spool. Alternatively, an opening might be formed into the side of the housing allowing winding and unwinding of the spool while positioned in the cavity. However, experimentation has shown that the configuration where the spool translates in and out of the cavity allows for easier winding and unwinding and also easy changing of the spool to another which may be freshly scented or alternatively scented.

The line wound on the spool is adapted for impregnation of liquid or powdered scent material thereon to the line directly and/or to absorbent components engaged to the line. Such scenting material may be imparted directly to the line prior to loading or while translated to project from the housing or through a sealable opening in the housing. Alternatively, spools having line pre-wound thereon may be pre-scented and then sealed in packages or containers for storage. The pre-scented spools can later be unpackaged and engaged upon the axle in the cavity for use.

Markers may be positioned at known distances from each other sequentially along the line. The markers are preferably easily discerned by humans, but not by animals, such as colorizing them in orange or another color not easily discerned by game animals. The markers on a deployed line can be employed by the user to discern a highly accurate distance assessment from the position of the user to any particular marker. Such provides for a significant enhancement of accuracy of the user aiming at a target adjacent any particular marker. The markers can also be formed of an absorbent material such as a polymer or ceramic to allow them to absorb scent material.

With respect to the above description, before explaining at least one preferred embodiment of the herein disclosed scent deploying device, it is to be understood that the invention is not limited in its application to the details of construction and to the arrangement of the components in the following description or illustrated in the drawings. The scenting invention herein described and shown is capable of other embodiments and of being practiced and carried out in various ways which will be obvious to those skilled in the art upon reading this disclosure. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other scent line deployment devices and for carrying out the several purposes of the present disclosed device. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

It is an object of the present invention to provide an easily deployable and retractable scenting device for use in hunting.

It is an additional object of this invention to provide such a scent device which is deployed as a scented line from a spool on which it may be recaptured after use.

It is a further object of this invention to provide such a spooled-line scenting device which includes spaced discernable distance markers allowing for enhanced targeting.

These and other objects, features, and advantages of the present scent line invention, as well as the advantages thereof over existing prior art, which will become apparent from the description to follow, are accomplished by the improvements described in this specification and hereinafter described in the following detailed description which fully discloses the invention, but should not be considered as placing limitations thereon.

BRIEF DESCRIPTION OF DRAWING FIGURES

The accompanying drawings, which are incorporated herein and form a part of the specification, illustrate some, but not the only or exclusive examples of embodiments and/or features of the disclosed scenting device. It is intended that the embodiments and figures disclosed herein are to be considered illustrative of the invention herein, rather than limiting in any fashion. In the drawings.

DETAILED DESCRIPTION OF THE INVENTION

In this description, the directional prepositions of up, upwardly, down, downwardly, front, back, top, upper, bottom, lower, left, right and other such terms refer to the device as it is oriented and appears in the drawings and are used for convenience only and such are not intended to be limiting or to imply that the device has to be used or positioned in any particular orientation.

Figure 1:
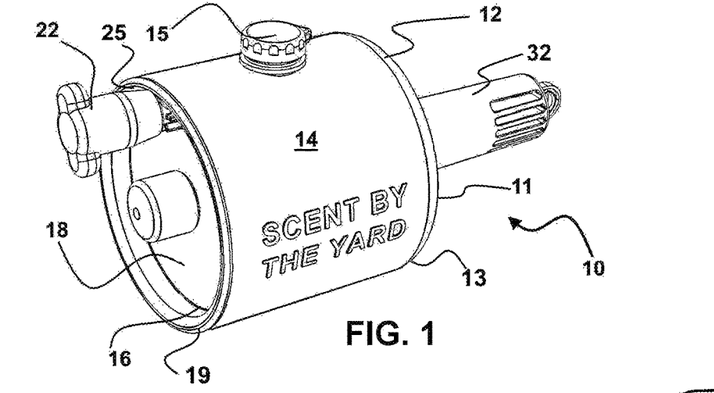
FIG. 1 depicts a perspective view of the housing of the device showing a handle engaged to the rotatable spool operatively engaged to a retracted or stored position within the housing.

Now referring to drawings in FIGS. 1-8, wherein similar components are identified by like reference numerals, there can be seen in FIG. 1 a perspective view of the scent device 10, showing the housing 12 which has a sidewall 14 extending from an endwall 11 at a first end 13 of the housing 12 to an opening 25 at a second end 19 of the housing 12. The opening 25 provides access to a cavity 16 of the housing 12 for translation into the retracted position shown in FIG. 1 to the deployed position of FIG. 3. In the deployed position, the spool 18 is translated through the opening 25 and out of the cavity 16 where it is positioned adjacent and extending away from the second end 19 of the housing 12, with all or a portion of the wound line 20 outside the cavity 16 and remains rotationally engaged with the housing 12. The spool 18 thus maintains a rotational engagement with the housing 12 while in the retracted position in the cavity 16 of the device 10 assembled for use, and while in this rotational engagement will also translate through the opening 25 from the cavity 16 and maintain the rotational engagement.

Figure 2:
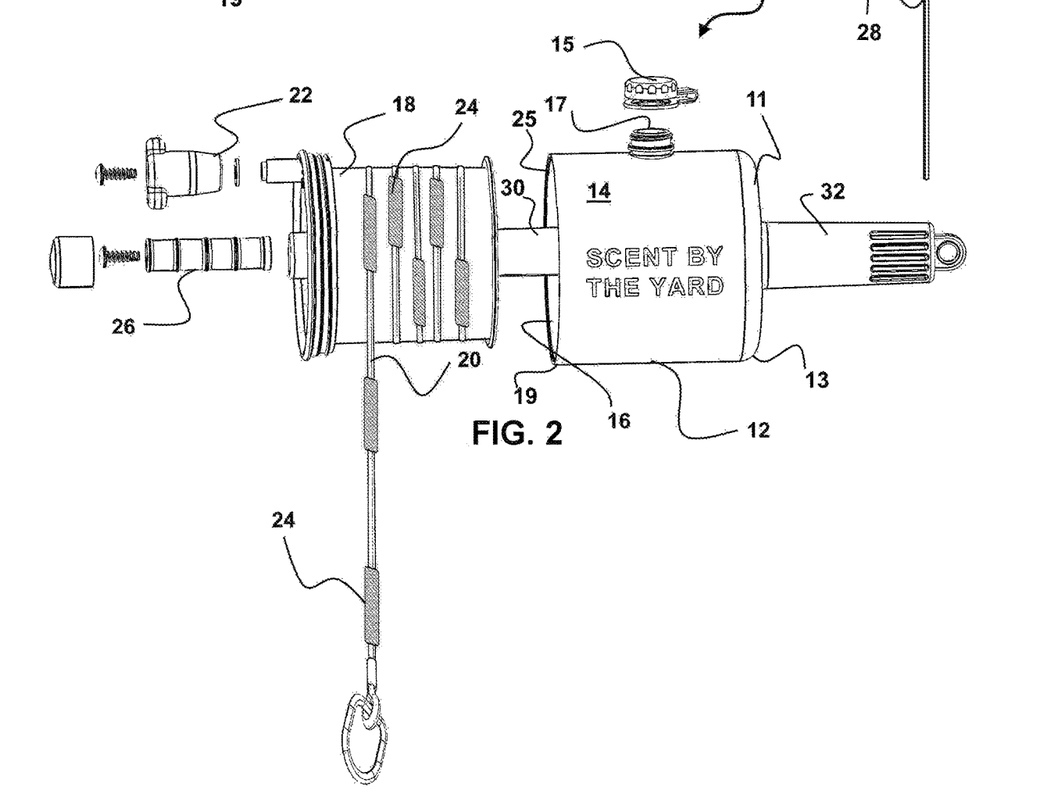
FIG. 2 depicts an exploded view of the components of FIG. 1 showing the handle-rotated spool having a scent line with discernable distance markers engaged thereto.
Figure 3:
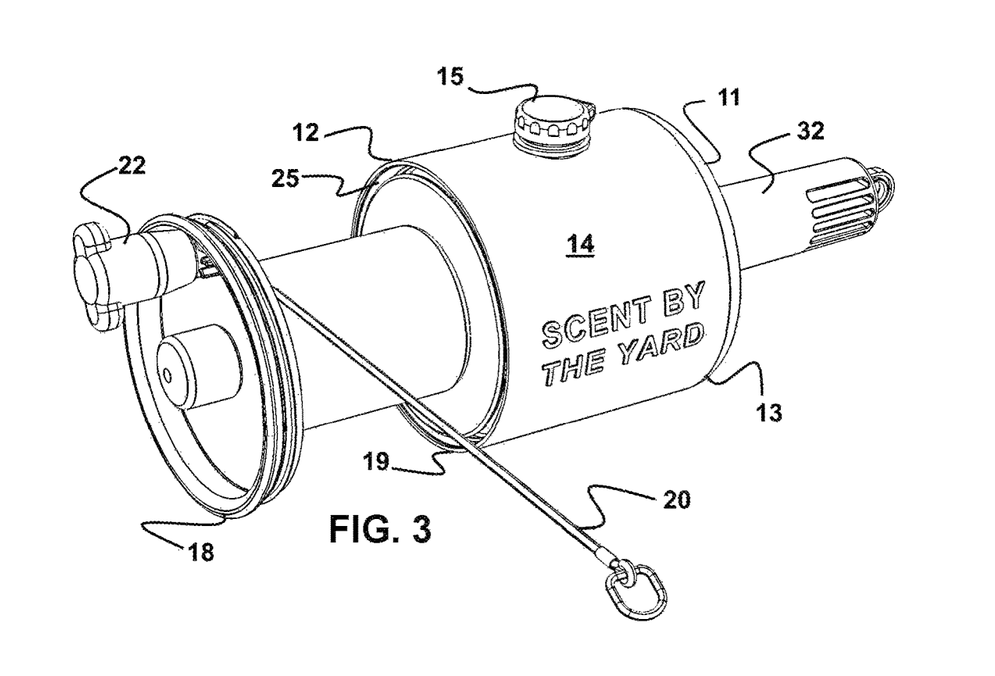
FIG. 3 shows the spool translated to a deployed position and depicting the scent line and spool positioned outside the cavity where it may be unwound to deploy it on the ground and rewound upon finishing and used for a subsequent deployment.
Figure 3A:
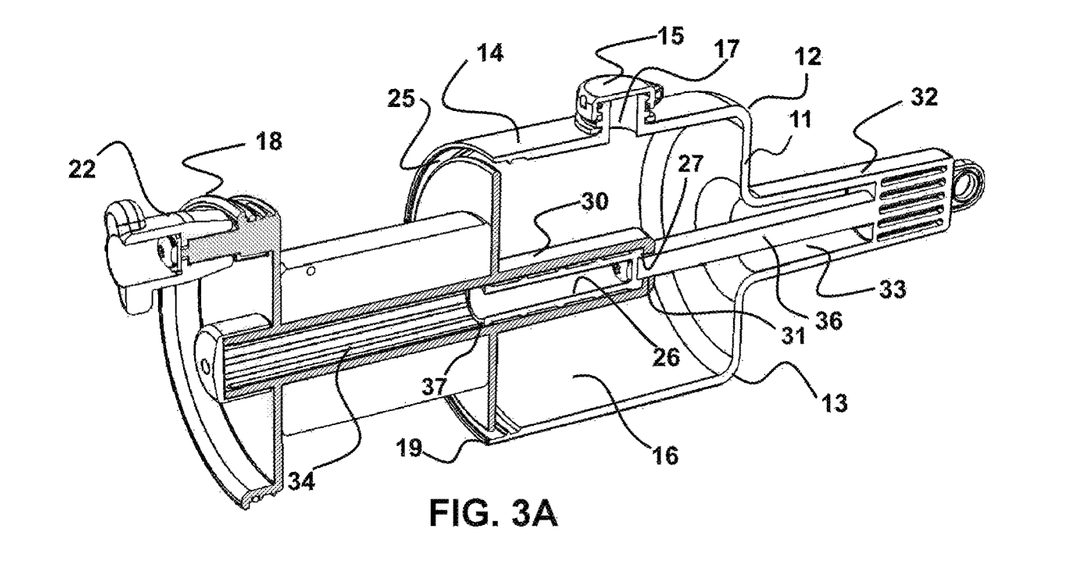
FIG. 3A depicts a sectional view of the device of FIG. 3 showing the translating rotating engagement of the spool with the housing enabling translation between the retracted position of FIG. 1 and the deployed position shown herein and in FIG. 3.

The spool 18, in this rotational engagement within the cavity 16 of the housing 12, is translatably engaged to slide between the retracted position within the cavity 16 as in FIG. 1, to the deployed position of FIG. 3, engaged to rotate on an axle 26 as shown in FIGS. 2 and 3A. The spool 18 thus will rotate when translated to the deployed position, with the spool 18 and all or a portion of the wound line 20 thereon, extending from the opening 25 of the cavity 16 shown in FIGS. 3 and 3A.

In the deployed position of FIGS. 3 and 3A, with the spool 18 projecting from the opening 25 at the second end 19 of the housing 12, the line 18 may be unwound from the rotationally engaged spool 18 to place the scented line 20 on the ground in the area desired by the user for hunting. A handle 22 is employable to rotate the spool 18 with an axial cavity 34 rotationally engaged to the axle 26 axially positioned in the cavity 16. The handle 22 is employable to rotate the spool 18 and rewind the line 20 thereon, once a use has finished, thereby allowing the line 20 and scent therein to be used many times.

In FIG. 2 is shown an exploded view of the main components of the device 10 of FIG. 1. Also shown, is the scent line 20 wound upon the spool 18 and having a plurality of visually discernable markers 24 engaged thereon. As shown and further discussed as in FIG. 5, the markers 24 are engaged to the line 20 at a known distance "D" from each other. The line 20 may be deployed on the ground in view of the user thereby positioning each of the plurality of spaced markers 24 in a spaced sequence. The deployed line 20 with markers 24 thereby forms a visually discernable distance gauge which the user, who can count the number of spaced markers 24, can determine a distance of each from the user's position for targeting purposes.

As shown in FIGS. 2 and 3A, a member 30 projects from a first end of the spool 18. This member 30 is sized for a translating engagement with a bearing member 36 axially extending in an axial passage 33 within a hollow projection 32 extending from the first end 13 of the housing 12 which communicates with the cavity 16.

As can be discerned from FIGS. 2 and 3A, sliding a spool 18 into the cavity 16 of the housing 12 from the second end 19 of the housing 12 engages the axial cavity 34 running through the spool 18 and member 30, in a translating and rotational engagement on the bearing member 36 extending through the axial passage 33 and axially through the cavity 16. This sliding engagement allows the user to translate the spool 18 from the retracted position in FIG. 1 to the deployed position shown in FIGS. 3 and 3A for dispensing and retrieving the line 20 from the spool 18.

It should be noted that in a simpler mode of the device 10 an opening such as with an aperture 17 shown in FIG. 2, could be formed in the sidewall 14 of the housing 12, and the spool 18 simply rotationally engaged within the cavity 16 during use. In this simpler mode, the line 20 can be unwound and rewound from the spool 18 while always positioned in the retracted position within the cavity 16. However, in experimentation, it was found to be much easier to wind and unwind the line 20 from the spool 18 when it is mounted to translate through the second end 19 of the housing 12 to a deployed position while the user gripped the exterior of the sidewall 14 which defines a grip for one hand of the user.

Providing the grip formed by the sidewall 14 and the translating spool 18, allowed for easy deployment for the user who simply holds the grip defined by the sidewall 14 in one hand, and letting the spool 18 unwind the line 20. The grip provided by the sidewall 14 also allowed the user to hold the housing 12 in one hand, while rotating the spool 18 in the deployed position of FIG. 2 using the handle 22 on the spool 18. Another advantage of line 20 providing the scenting herein is that the line 20 once deployed can then be dragged upon the ground to leave an uninterrupted scent in a trail leading to the final positioning of the line 20 on the ground. This allows for additional scenting of the area along a linear path which is continuous.

It was found in experimentation that to try and hold the spool 18 by the grip formed by the sidewall 14, in a fixed rotational spool 18 in the cavity 16 with the line 20 extending through an aperture 17 during deployment and retrieval, was not as easy to accomplish. Further, the scent material from the line 20 was continually deposited on the gripping hand of the user, and worse, the line 20 frequently was contaminated by the scent of the user when it touched their hand or person during unwinding through an aperture 17 in the sidewall 14 being gripped, which is not desirable because game will almost always avoid a human scent and the area around it.

As such, the most preferred mode of the device 10 positions the spool 18 in a translating engagement shown in FIG. 3A, for example. In this preferred mode, the spool 18 is supported and rotatable when translated to a deployed configuration of FIG. 2 or FIG. 3 whereby the user uses the sidewall 14 as a grip for one hand and does not come into contact with the line 20.

Also shown in FIGS. 1-3A, are a removable cap 15 which provides access to the covered aperture 17 communicating into the cavity 16. Liquid scent may be deposited through the aperture 17 and onto the line 20 wound on the spool 18 while in the retracted position within the cavity 16 of the housing 12. The cap 15 may then be re-engaged to seal the aperture 17 and maintain the scent within the cavity 16.

As can be seen in FIGS. 3-3A, the spool 18 is both rotationally and translatably engaged upon a bearing member 36 extending axially through the axial passage 33 of the projecting member 30. The bearing member 36 is engaged at a first side thereof with the housing 12 at a first end of the housing 12 and extends to a distal end located adjacent the opening 25 at the second end of the housing 12.

Shown in FIG. 3A, the axle 26 is engaged at a first end to the bearing member 36 and extends to a distal end of the axle 26 located adjacent the opening 25. As noted herein, the bearing member 36 can extend itself to a distal end without the inclusion of the engaged axle 26, however it is preferred to include the axle 26 engaged to and forming part of the bearing member 36 so it may be replaced if it becomes worn. The inclusion of the engaged axle 26 is also preferred because a shoulder 27 is formed on the bearing member 36, which limits the distance of travel of the spool 18 during translation out of the opening 25 to the deployed position.

While the axle 26 is shown engaged with the bearing member 36, the bearing member 36 itself could serve as the axle 26. As can be best discerned in FIG. 3A, the spool 18 is slidable from the retracted positioning of FIG. 1, with the line 20 sealed within the cavity 16 of the housing 12 when not in use, to a deployed position of FIG. 3, where the spool 18 will rotate on the axle 26 or bearing member 36 to allow unwinding of the line 20 as it is placed on the ground.

Also shown in FIG. 3A, a passage 31 at the open end of the hollow member 30 extending from the spool 18, is sized with a passage diameter sized to contact and slide on the bearing member 36 but which is smaller than a diameter of the shoulder 27 whether formed at the engagement of the axle 26 or by just a shoulder 27 portion extending around the circumference of the bearing member 36, which has a larger diameter than the passage 31. Thus, a contact of the passage 31 with the shoulder 27 when the spool 18 is moved to the deployed position limits travel of the spool 18 and prevents a dismount.

Additionally, the shoulder 27 could also be formed by a wider shoulder portion of the bearing member 36 which has a diameter extending past the diameter of the bearing member 36 and which is a single piece without the axle 26. In this mode the passage 31 may be formed of elastic material adapted to expand and slide over the shoulder 27 on engagement of a spool 18. Further, by adjacent the opening 25 for the distal end 37 is meant that the distal end 37 of the bearing member 36 whether formed by a connected axle 26 or a unitary bearing member 36 is positioned either aligned with the opening 25 at the second end 19 of the housing 12 or slightly out of such alignment but within substantially inch thereof.

Figure 4:
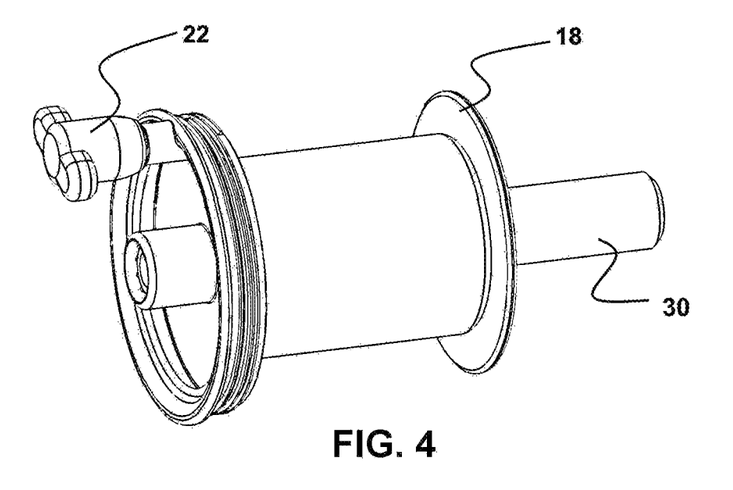
FIG. 4 shows a spool adapted to rotationally engage within the housing and translate between retracted and deployed positions and which may be sold separately with scented line thereon or stored and used within a housing.
Figure 8:
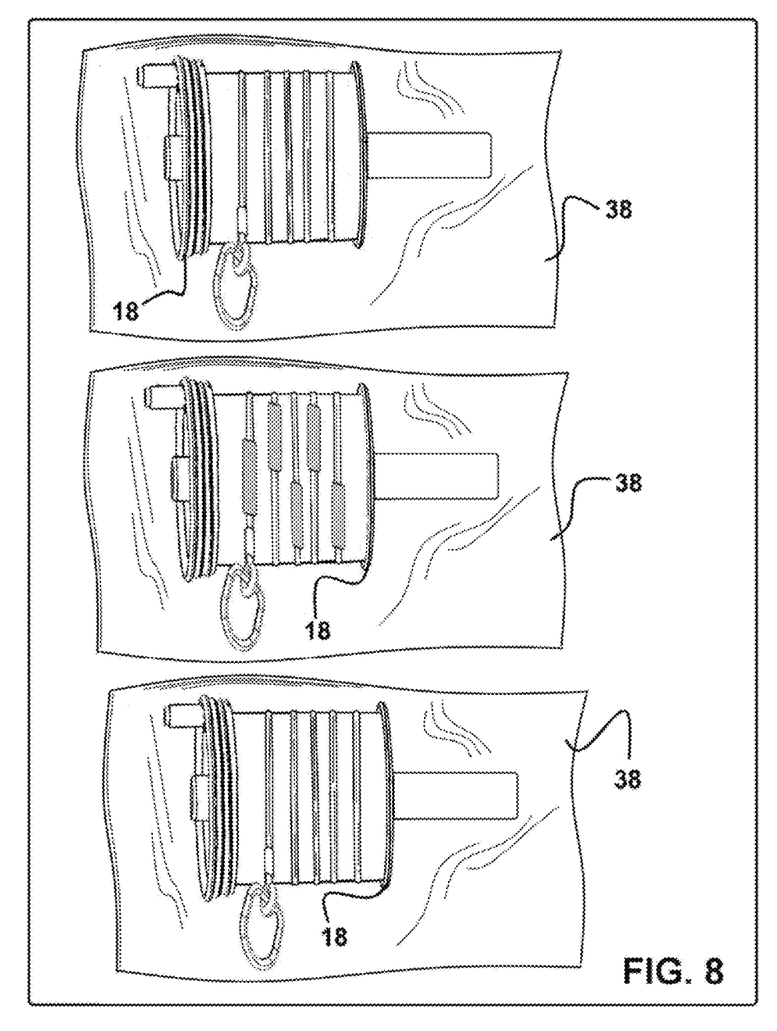
FIG. 8 shows a kit of spools with each sealed in a package and which may have different or varied scents on the line of the spool allowing the user to engage any chosen one of the plurality of spools in the kit to a housing.

Shown in FIG. 4 is the spool 18 which may also be provided separately from the housing 12 or sold in a kit of a plurality of spools 18 such as in FIG. 8, where each is operatively engageable with the housing 12. In this mode of the device 10, the spools 18 can be provided in sealed packages 38 such as in FIG. 8, or stored in sealed containers with a desired scent impregnated to a line 20 wound on the spool 18. This allows scented spools 18 to be used with the device 10 to be sold separately in stores where users would be able to buy speciality scented lines 20 pre-wound on spools 18 which would then be engaged for translating rotational engagement with the housing 12. Such would allow for the development of scents for regional use or with secret or proprietary scent ingredients which can be provided on spools 18 sealed in packages and ready to use.

Figure 5:
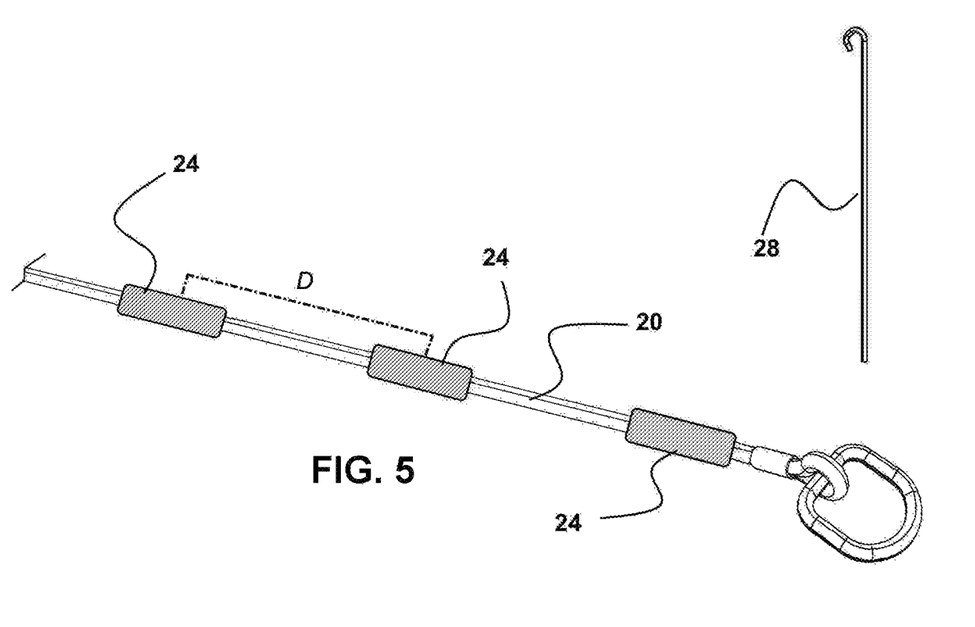
FIG. 5 depicts the scented line showing visually discernable markers engaged thereto a defined distance "D" from each other and used to ascertain a distance from the user.

Shown in FIG. 5 is a depiction of the line 20 which as noted above, is formed of material adapted to absorb or be impregnated with scent in liquid or powder or other forms. Such line might be formed of natural fibers, felt, absorbent synthetic materials, or the like adapted to have scent imparted thereto either in the prepackaged mode shown in FIG. 8, or in a mode where squirting scent material is communicated to the line 20 through the aperture 17 into the cavity 16.

Also shown in FIG. 5, the markers 24 are depicted as spaced an equal distance "D" from each other sequentially. Thus, a user, by counting the number of markers 24 extending along the line 20 from their position, can count and use the markers 24 on the line 20 as a gauge to discern the exact distance from their position to any particular marker 24. Such sequentially positioned markers 24 at fixed positions and substantially equal distances "D" from each other, thus, provide a significant aid to users in discerning a distance from their position to enhance their targeting proximate to a marker 24. By substantially equal is meant plus or minus 10 percent in distance in the fixed positioning as might occur during manufacturing.

Further, the markers 24 might be colorized or otherwise marked to signify known distances from the user, which would allow determination of a distance to such markers 24 by knowing the distance a color or pattern signifies. The markers 24 may be ceramic material or polymeric material or plastic material or metal or another material adapted for colorization and durability. If formed of ceramic or polymeric material such may be absorbent so scent can be imparted to the markers 24. Securement of one end of the line 20 to the ground can be provided by a pin 28 or the line through an opening formed on the distal end of the line 20.

Figure 6:
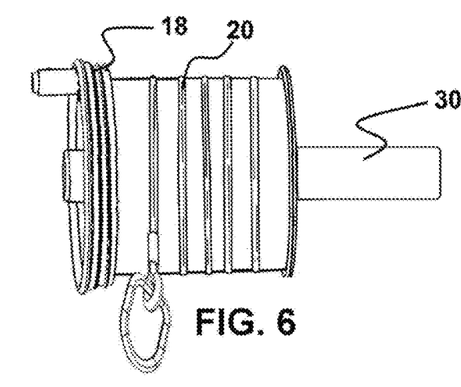
FIG. 6 shows a spool having line wound thereon which may be scented with liquid or powder or other scent material which will cling to or be absorbed by the line.

Shown in FIG. 6, is a spool 18 which as noted may be provided with the device 10 herein, solely with line 20 wound thereon. As noted, the line 20 is formed of material which may be scented with liquid or powder or other scent material which will cling to or be absorbed by the line 20.

Figure 7:
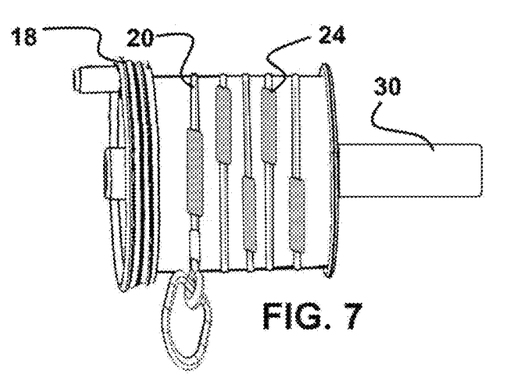
FIG. 7 shows a spool similar to that of FIG. 6 but which includes markers engaged sequentially along the line which are spaced at predetermined distances to provide a user a visually discernable distance marker allowing the user to discern a distance of each marker from the start to the finish of the deployed line.

As shown in FIG. 7, the spool 18 can also be provided with line 20 similar to that of FIG. 6 but where markers 24 are engaged sequentially along the line 20. As noted, the markers 24 may be spaced at predetermined substantially equal distances from each other to form a gauge which is visually discernable by the user with the line 20 deployed on the ground. Such allows the user to calculate a distance of each marker 24 from the start of the line 20 to any one of the markers 24 positioned on the deployed line 20.

Finally, as shown in FIG. 8, the device 10 herein may be provided with a kit formed of a plurality of spools 18 with each sealed in a package 38. Such may be provided with the device 10 on purchase, and/or the kit may be made available to users of the device 10 for replenishment of a scent being used, or to easily and quickly change the scent being used on a line 20 to be deployed. Thus, the plurality of spools 18 in the kit may be made available with different or varied scents on the line 20 of each spool 18 allowing the user to engage any one of the plurality of spools 18 in the kit to a housing 12.

It should be noted that any of the different depicted and described configurations and components of the spooled scent deployment device herein can be employed with any other configuration or component shown and described as part of the device herein. Additionally, while the present invention has been described herein with reference to particular embodiments thereof and steps in the method of production, a latitude of modifications, various changes and substitutions are intended in the foregoing disclosures, it will be appreciated that in some instance some features, or configurations, of the invention could be employed without a corresponding use of other features without departing from the scope of the invention as set forth in the following claims. All such changes, alternations and modifications as would occur to those skilled in the art are considered to be within the scope of this invention as broadly defined in the appended claims.

Further, the purpose of any abstract of this specification is to enable the U.S. Patent and Trademark Office, the public generally, and especially the scientists, engineers, and practitioners in the art who are not familiar with patent or legal terms or phraseology, to determine quickly from a cursory inspection the nature and essence of the technical disclosure of the application. Any such abstract is neither intended to define the invention of the application, which is measured by the claims, nor is it intended to be limiting, as to the scope of the invention in any way.

What is claimed is:

1. A scent dispensing apparatus, comprising:
   a housing having a sidewall extending between a first end and a second end of said housing;

said sidewall surrounding a cavity;
an opening at said second end of said housing communicating with said cavity;
a bearing member having a first side thereof engaged with said housing, said bearing member extending into said cavity to a distal end;
a spool, said spool having a scented line wound thereon;
said spool in a rotational engagement upon said bearing member;
said spool in a sliding engagement with said bearing member, said sliding engagement running between said first side of said bearing member and a shoulder portion at or adjacent said distal end of said bearing member;
said spool having a retracted position wherein said spool is positioned within said cavity;
said spool translatable upon said bearing member through said opening to a deployed position extending past said second end of said housing wherein it is held in said rotational engagement by said shoulder portion; and
said scented line positionable on a ground surface to a used position of said line, by an unwinding from said spool while in said deployed position.

2. The scent dispensing apparatus of claim 1, additionally comprising:
said rotational engagement comprising a rotational engagement of an axial cavity of said spool upon said bearing member communicating axially through said cavity, said bearing member engaged at said first side thereof, with said first end of said housing, said bearing member extending to said distal end thereof which is located in-between said first end and said second end of said housing.

3. The scent dispensing apparatus of claim 2, additionally comprising:
a plurality of spools;
said spool being one of said plurality of said spools;
said scented line on each respective one of said plurality of spools having a different individual scent from others of said plurality of spools, whereby a user can choose an individual said spool from said plurality of spools having a said individual scent desired by said user.

4. The scent dispensing apparatus of claim 2, additionally comprising:
a plurality of markers sequentially positioned upon said line to fixed positions thereon;
each of said plurality of markers being substantially equally spaced from adjacent markers from said plurality of markers; and
said plurality of markers defining a distance gauge with said line in said used position, whereby a user can calculate a distance to any of said plurality of markers.

5. The scent dispensing apparatus of claim 2, additionally comprising:
a projection portion formed into said first end of said housing, said projection portion extending in a direction away from said cavity, said projection portion having an axial passage communicating with said cavity;
said first end of said bearing member engaged to said first end of said housing within said projection portion,
said bearing member axially disposed in said axial passage and extending into said cavity;
a member extending from a first end thereof engaged with a first side of said spool, to a second end of said member having a passage therein;
and axial cavity extending through said spool and said member and communicating with said passage;
said passage in a sliding engagement upon said bearing member;
said member positioned within said axial passage of said projection portion with said spool in said retracted position;
and
said passage having a passage diameter smaller than said diameter of said shoulder portion, whereby a contact of said passage with said shoulder portion limits translation of said spool when moved to said deployed position.

6. The scent dispensing apparatus of claim 5, wherein said rotational engagement comprises:
an axle engaged to said bearing member at a first end of said axle;
said axle sized for a rotational positioning upon said bearing member; and
said first end of said axle defining said shoulder portion.

7. The scent dispensing apparatus of claim 5, additionally comprising:
a plurality of markers sequentially positioned upon said line to fixed positions thereon;
each of said plurality of markers being substantially equally spaced from adjacent markers from said plurality of markers; and
said plurality of markers defining a distance gauge with said line in said used position, whereby a user can calculate a distance to any of said plurality of markers.

8. The scent dispensing apparatus of claim 6, additionally comprising:
a plurality of markers sequentially positioned upon said line to fixed positions thereon;
each of said plurality of markers being substantially equally spaced from adjacent markers from said plurality of markers; and
said plurality of markers defining a distance gauge with said line in said used position, whereby a user can calculate a distance to any of said plurality of markers.

9. The scent dispensing apparatus of claim 1, additionally comprising:
a plurality of markers sequentially positioned upon said line to fixed positions thereon;
each of said plurality of markers being substantially equally spaced from adjacent markers from said plurality of markers; and
said plurality of markers defining a distance gauge with said line in said used position, whereby a user can calculate a distance to any of said plurality of markers.

10. The scent dispensing apparatus of claim 9, additionally comprising:
a plurality of spools;
said spool being one of said plurality of said spools;
said scented line on each respective one of said plurality of spools having a different individual scent from others of said plurality of spools, whereby a user can choose an individual said spool from said plurality of spools having a said individual scent desired by said user.

11. The scent dispensing apparatus of claim 1, additionally comprising:
a plurality of spools;
said spool being one of said plurality of said spools;
said scented line on each respective one of said plurality of spools having a different individual scent from others of said plurality of spools, whereby a user can choose an individual said spool from said plurality of spools having a said individual scent desired by said user.

\* \* \* \* \*